US00PP35725P2

(12) United States Plant Patent
Hansen

(10) Patent No.: US PP35,725 P2
(45) Date of Patent: Apr. 2, 2024

(54) ***SEDUM* PLANT NAMED 'MIDNIGHT VELVET'**

(50) Latin Name: ***Sedum* hybrid**
Varietal Denomination: Midnight Velvet

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 18/445,124

(22) Filed: Apr. 17, 2023

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Susan McCormick Ewoldt

(57) ABSTRACT

A new and distinct ornamental perennial *Sedum* plant named 'Midnight Velvet' is characterized by tight-forming domed mounds with vertical stems producing rich dark-purple leaves. The deep wine-colored stems are highly branched and resist lodging in the summer heat and rains. Numerous mauve flower buds open to show off deep-rose flowers nearly completely covering the top of the plant and later display the dark red carpels. The new plant is useful for the landscape in containers, as specimens or en masse.

2 Drawing Sheets

Botanical designation: *Sedum* hybrid.
Cultivar denomination: 'Midnight Velvet'.

STATEMENT REGARDING PRIOR DISCLOSURES UNDER 37 CFR 1.77(B)(6)

The claimed plant was first sold or offered for sale by Walters Gardens, Inc. to Quality Greenhouse on Jul. 13, 2022, by Walters Gardens, Inc., who obtained the plant and all information relating thereto, from the inventor. Subsequently, on Feb. 1, 2023, the plant was featured in a non-enabling disclosure of a brief description and photograph on a website operated by Walters Gardens, Inc. No plants of *Sedum* 'Midnight Velvet' have been sold in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of *Sedum* plant, botanically known as *Sedum* and hereinafter referred to by the cultivar name 'Midnight Velvet' or the new plant.

The new *Sedum* plant is a selection of a planned breeding program conducted by the inventor, at a wholesale perennial nursery in Zeeland, Michigan, USA.

The new *Sedum* plant was selected as a single seedling from an insect pollination of the proprietary unnamed seedling referred to only by the breeder code 14-30-1 (not patented) at a wholesale perennial nursery in Zeeland, Michigan. The parent was placed amongst other seedlings and cultivars on about Sep. 1, 2015, and the seed was collected in the fall of the same year. *Sedum* 'Midnight Velvet' was assigned the breeder code number 15-19-9 to keep it separated from thousands of other seedlings of this and other crosses when it progressed through the initial trial phase in the fall of 2016. The selected single seedling clone was originally selected for its strong, healthy, dense growth, colorful foliage and flowers, and intermediate traits between the two parents.

Asexual reproduction of *Sedum* 'Midnight Velvet' by division at a wholesale perennial nursery in Zeeland, Michigan, USA since October of 2017 and subsequent vegetative shoot tip cuttings has shown that the unique features of this new *Sedum* plant are stable and reproduced true to type in successive generations of asexual propagation.

SUMMARY OF THE INVENTION

Plants of *Sedum* 'Midnight Velvet' have not been observed under all possible environmental conditions. The phenotype may vary somewhat with variations in environment such as temperature, available water, fertility, and light intensity without, however, any variation in genotype.

The following traits have been repeatedly observed and are determined to comprise the unique characteristics of *Sedum* 'Midnight Velvet' and distinguish it as a new and distinct stonecrop plant unique from all other stonecrop plants known to the inventor:

1. Tight-forming, large, domed mounds with vertical stems;
2. Center stems remain erect throughout the growing season producing full habit;
3. Foliage is rich dark-purple in high UV light exposure and gray-green with purplish highlights in more shade or where protected from UV light;
4. Numerous mauve flower buds develop to deep rose-colored flower clusters completely covering the plant beginning in mid-August.
5. Flowers later take on a dark reddish color produced by the carpels.

In comparison with the female parent, the new plant has a taller and broader habit with darker purple foliage and deeper rose-red flowers.

The nearest comparison varieties known to the inventor are: 'Night Embers' U.S. Plant Pat. No. 29,211, 'Back in Black' U.S. Plant Pat. No. 33,632, 'Black Jack' U.S. Plant Pat. No. 16,736, 'Night Light' U.S. Plant Pat. No. 34,272, and 'Peach Pearls' (not patented).

'Night Embers' has foliage that is less glaucous and more glossy and darker burgundy, the habit is tighter, more upright, and less mounded, and the flowers are light mauve-pink. 'Back in Black' is slightly taller in habit, with darker foliage and the flowers produce light rose petals. 'Black Jack' is slightly shorter and broader in habit, with darker burgundy foliage that is more susceptible to powdery mildew, and the flowers produce purplish-red to purplish-pink petals. 'Night Light' has a habit of tall tight-fitting mounds, the foliage is smaller and olive-green with greyed purple, and the flowers are light yellow that mature to pink with deep-rose carpels. 'Peach Pearls' has a more upright and less mounded habit, with flowers that begin creamy-colored and the carpels develop to more bronzy red with seed.

The parent, 14-30-1, has not been maintained and no comparison is possible.

BRIEF DESCRIPTION OF THE PHOTOGRAPHS

The photograph of the new plant demonstrates the unique traits and the overall appearance of *Sedum* 'Midnight Velvet'. The colors are as accurate as reasonably possible with color reproductions of this type. Variations in ambient light spectrum, source, and direction may cause the appearance of minor variations in color. The plants used in the photograph were four-year-old plants grown in an open, full-sun trial garden at a wholesale perennial nursery in Zeeland, Michigan with supplemental water and fertilizer when needed. No plant growth regulators or pinching have been used.

DETAILED BOTANICAL DESCRIPTION

Figure 1:
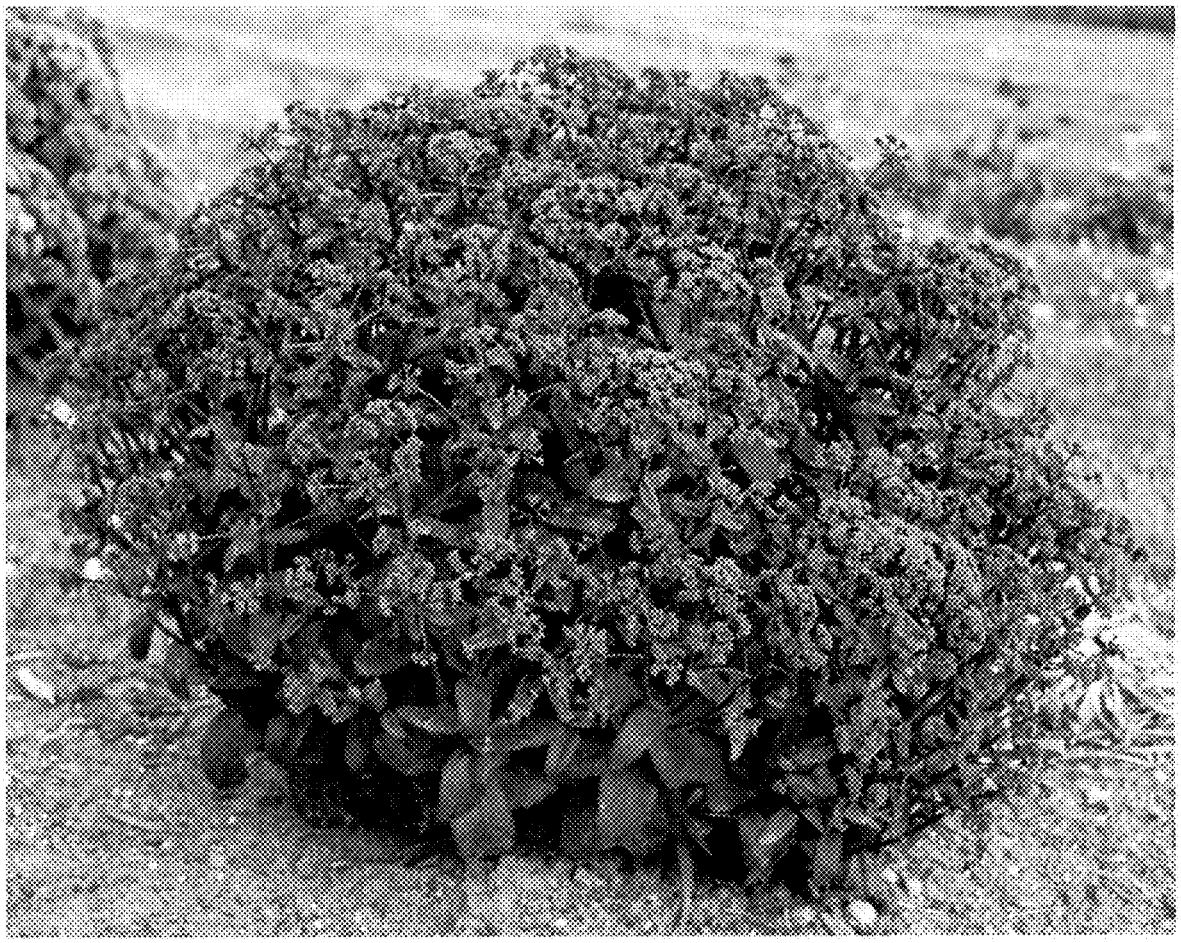
FIG. 1 shows the habit of the new plant with foliage in the early stages of flowering.
Figure 2:
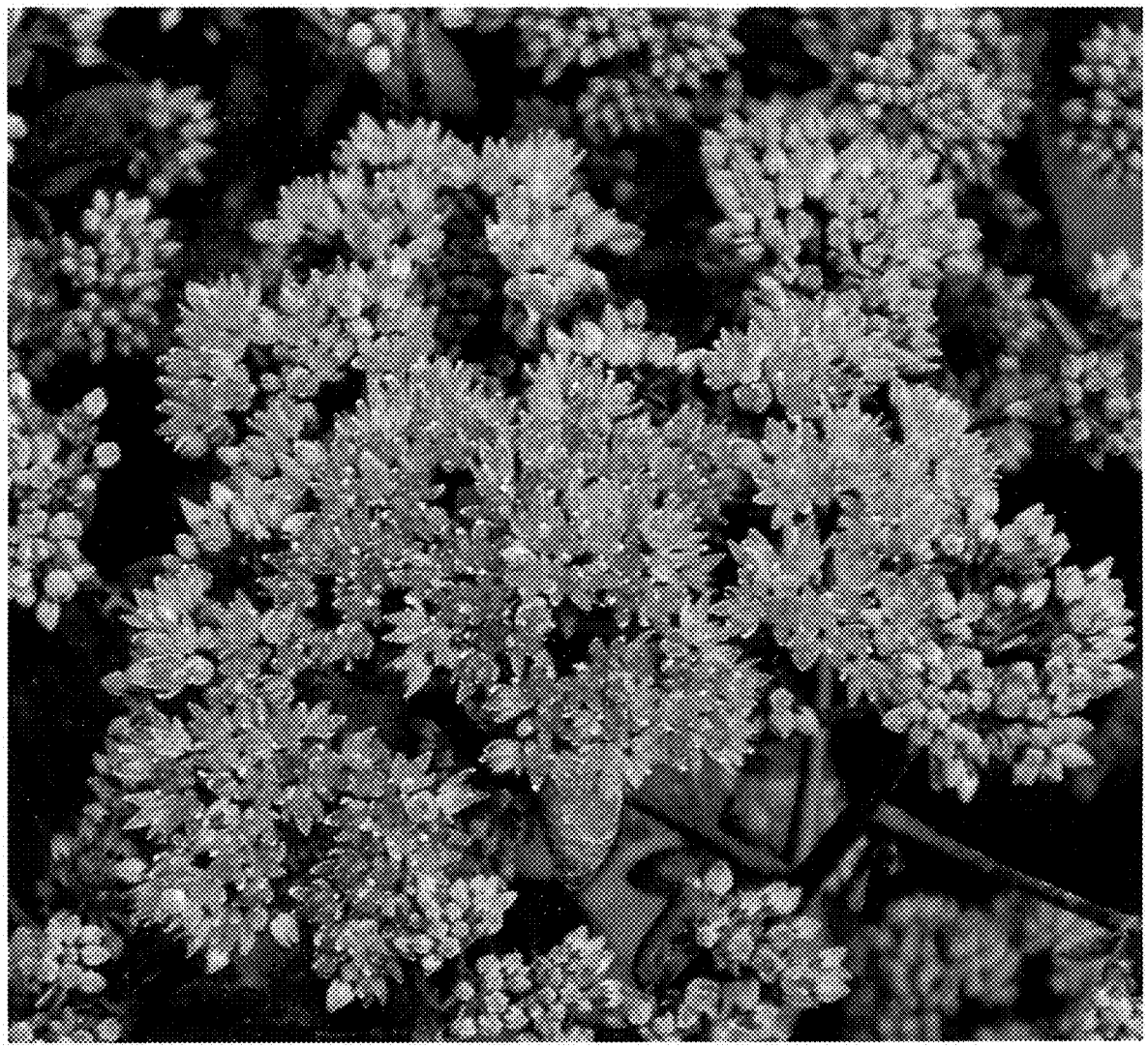
FIG. 2 shows a close-up of the flowers and buds of the new plant in mid-summer.

The following is a detailed description of two-year-old plants of the new cultivar as grown outdoors in a full sun trial plot and in a partially shaded greenhouse at a wholesale nursery in Zeeland, Michigan. No plant growth regulators have been used. Plants of the new cultivar have not been tested under all possible conditions. The phenotype may vary with changes in the environment, climate, and cultural conditions without a change in the genotype. The color reference is in accordance with the 2015 edition of The Royal Horticultural Society Colour Chart except where general color dictionary terms are used.

Botanical designation: *Sedum* hybrid;

Cultivar denomination: 'Midnight Velvet';

Parentage: The female parent is an unnamed proprietary hybrid known only by the breeder code 14-30-1; the male parent is unnamed, but may have been any one of a number of other siblings, seedlings, or cultivars in the isolation block hybridizing area;

Asexual propagation: Stem tip cuttings and division;

Time to initiate roots: About two weeks;

Time to finish a 3.8-liter flowering container: About three months in the summer from a rooted 2.5 cm plug;

Root description: Thick, fleshy; freely branching; creamy white to light tan in color depending on soil composition;

Plant habit: Winter-hardy herbaceous perennial; upright mound; stiff upright stems; dense and full, not opening in center later in the season; flower heads densely and freely branching;

Growth rate: Moderately vigorous;

Plant size: About 36 cm tall and 48 cm wide in full flower;

Stems: Terete; glaucous; glabrous; diameter at base to about 9 mm, average about 7 mm; heavily branched in distal flowering portion; about 15 cm long from base to initial branches; about 12 stems per plant and 12 branches per stem;

Stem color: Proximally or in shade nearest RHS 147C, distally nearest between RHS N187B and RHS N186B;

Lateral branches: To about 10 per stem; glaucous; glabrous; terete; primary branches to about 18 cm long and about 5 mm diameter at base;

Lateral branch color: Between RHS 187A and RHS N186C;

Foliage: Ovate; opposite; simple; smooth; sarcous; glabrous and glaucous on both surfaces; sessile; thick; apex bluntly acute to rounded; base attenuate to rounded; margin irregularly and shallowly dentate, 7 to 10 teeth; teeth about 1 mm long and 2 mm wide, to 12 mm apart; decreasing in size distally; attitude outward; to about 34 per stem, lower leaves not always persistent;

Foliage size: To about 9 cm long, 6 cm across, and 3 mm thick at midrib; average about 5.5 cm long, 4.2 cm across, and 3 mm thick; decreasing distally;

Foliage color: Adaxial young nearest RHS NN137B with slight blush between RHS N186B and RHS N186C, abaxial young between RHS N138B and RHS 147B; mature adaxial nearest RHS N187A, abaxial between RHS 191A and RHS N138C variably blushed with nearest RHS N187A;

Petiole: Leaves sessile;

Venation: Palmate, barely distinguishable; glabrous; glaucous; matte adaxial and slightly lustrous abaxial; slightly raised abaxial;

Vein color: Adaxial midrib between RHS N187A and RHS N186B, abaxial midrib nearest RHS 146C with variable blushing of nearest RHS N186B; secondary veins not obvious;

Flower buds about one day prior to opening: Ellipsoidal; apex acute; base truncate; about 4 mm long and about 2.5 mm diameter near middle;

Flower bud color: Petals between RHS 186A and RHS N186D; calyx nearest RHS N138B;

Flower: Stellate, actinomorphic; imperfect, pistillate; pentamerous; persistent; attitude upright to outwardly in terminal compound cymes;

Flower size: Size to about 5.5 mm across at petal apices and 5 mm tall, average about 4.5 mm across and 4.5 mm tall;

Flower number: To about 100 to 200 per branch and 1,500 to 3,000 flowers per stem and 10,000 to 15,000 per plant;

Fragrance: None detected;

Flowering season: Beginning mid-summer in Zeeland, Michigan for about four weeks;

Longevity: Flower cymes remain effective for about four weeks on the plant and one to one and a half weeks as cut flowers; individual flowers and calyces persistent and effective for about two weeks;

Inflorescence: To about 18 cm tall from below the first branch to the top, and about 20 cm across;

Petals: Typically five; lanceolate; glabrous; narrowly acute apex; fused base; entire margin; slightly involute; glabrous and slightly glaucous both abaxial; to about 3 mm long and 1.5 mm wide;

Petal color: Young flowers adaxial and abaxial nearest RHS N155D with a blush randomly concentrated of nearest RHS 185B; before dehiscing becoming translucent to nearest RHS 195D;

Calyx: With five sepals; campanulate to stellate; average about 3 mm across and 2 mm deep;

Sepals: Linear to lanceolate; narrowly acute apex; fused base; entire margin; slightly involute; glabrous, and slightly lustrous both abaxial; adpressed to petals, to about 2 mm long beyond fusion and about 1 mm across at base;

Sepal color: Nearest RHS 146A with light to moderate blush of nearest RHS N186C where exposed to high ultraviolet light;

Peduncles: Terete; glaucous, glabrous, becoming lustrous; stiff and flexible; freely and heavily branching; mostly upwardly to slightly outwardly; with branches and branchlets to about 45° above horizontal; to about 18 cm long and 8 mm diameter at base;

Peduncle color: Nearest RHS 146C, and with exposure to high ultraviolet light between RHS N186C and RHS 187A;

Pedicels: Cylindrical; glabrous; glaucous, becoming lustrous; strong and stiff, yet flexible; to about 3 mm long and 0.7 mm diameter; average about 2.5 mm long and 0.5 mm diameter;

Pedicel color: Between RHS N186C and RHS 187A;

Androecium: Not observed, absent;

Gynoecium: Typically five; cylindrical, conical in distal one-third; to about 4 mm long and 1.2 mm diameter near middle;

*Style*.—Terete conical; tapering distally with base truncate; about 1 mm long and 0.5 mm diameter at point of attachment to ovary; glabrous; lustrous; color initially upon opening nearest RHS 59A, progressing to nearest RHS 60C at maturity.

*Stigma*.—Minute, acute; about 0.2 mm diameter and 0.2 mm long; color nearest RHS 60C at maturity.

*Ovary*.—Conical; acutely tapering at apex to style; base truncate; lustrous; about 4.0 mm long and 1.5 mm diameter; color initially upon opening nearest RHS 59A, progressing to nearest RHS 60C at maturity.

Fruit and seed: Not observed;

Growing conditions: Plants of the new *Sedum* 'Midnight Velvet' is xeromorphic and grow best with good drainage, full sun and moderate to low fertility. 'Midnight Velvet' tolerates heavy rains and wind and is not prone to develop an open center later in the season as many other *Sedum* cultivars do that are known to the inventor.

Hardiness: The new plant is cold-hardy from USDA zones 3 to 9 and has tolerated temperatures of at least 35 degrees C.

Disease and pest resistance: Pest and disease susceptibility, resistance, and tolerance outside that normal for *Sedum* is not known.

It is claimed:

1. A new and distinct perennial *Sedum* plant named 'Midnight Velvet' as herein described and illustrated.

* * * * *